(12) United States Patent
Jung

(10) Patent No.: US 10,952,660 B2
(45) Date of Patent: Mar. 23, 2021

(54) BERG BALANCE TESTING APPARATUS AND METHOD FOR THE SAME

(71) Applicant: MAN & TEL Co., Ltd., Gumi-si (KR)

(72) Inventor: Kwang Wook Jung, Gumi-si (KR)

(73) Assignee: MAN & TEL Co., Ltd., Gumi-si (KR)

( * ) Notice: Subject to any disclaimer, the term of this patent is extended or adjusted under 35 U.S.C. 154(b) by 318 days.

(21) Appl. No.: 16/114,229

(22) Filed: Aug. 28, 2018

(65) Prior Publication Data

US 2019/0200911 A1    Jul. 4, 2019

(30) Foreign Application Priority Data

Dec. 28, 2017   (KR) .................... 10-2017-0182428

(51) Int. Cl.
   *A61B 5/00*      (2006.01)
   *A61B 5/11*      (2006.01)
   *A61B 5/103*     (2006.01)

(52) U.S. Cl.
   CPC .......... *A61B 5/4023* (2013.01); *A61B 5/1036* (2013.01); *A61B 5/11* (2013.01); *A61B 5/743* (2013.01); *A61B 5/7435* (2013.01); *A61B 5/7475* (2013.01)

(58) Field of Classification Search
   CPC .... A61L 35/11; A61L 35/1102; A61L 35/112; A61L 35/1036; A61L 35/4023; A61L 35/743; A61L 35/7435
   USPC ....................................................... 600/595
   See application file for complete search history.

(56) References Cited

U.S. PATENT DOCUMENTS

| | | | |
|---|---|---|---|
| 6,231,527 B1 * | 5/2001 | Sol ........................ | A61B 5/1038 348/143 |
| 9,110,089 B2 * | 8/2015 | Weyand ................ | A61B 5/1114 |
| 9,202,386 B2 * | 12/2015 | Yuasa .................. | A61B 5/1036 |
| 9,494,446 B2 * | 11/2016 | Murray ................. | G01C 22/00 |
| 9,526,451 B1 * | 12/2016 | Berme ............... | A63B 24/0062 |
| 9,622,686 B1 * | 4/2017 | Berme ............... | A63B 22/0292 |
| 9,974,478 B1 * | 5/2018 | Brokaw ................ | A61B 5/486 |
| 2008/0306412 A1 * | 12/2008 | Nieminen ............ | A61B 5/1121 600/595 |
| 2011/0190593 A1 * | 8/2011 | McNair ................ | A61B 5/6831 600/300 |
| 2011/0288811 A1 * | 11/2011 | Greene ................ | A61B 5/1123 702/141 |
| 2015/0282766 A1 * | 10/2015 | Cole .................... | A61B 5/7267 702/139 |

(Continued)

FOREIGN PATENT DOCUMENTS

KR   10-2002-0095314 A   12/2002

*Primary Examiner* — Max F Hindenburg
(74) *Attorney, Agent, or Firm* — Revolution IP, PLLC

(57) ABSTRACT

A berg balance testing apparatus includes: a floor frame that is a stage on which the examinee takes movements; a plurality of first sensors that is disposed in sections divided to have a predetermined area on the floor frame and senses positions of the feet of the examinee; a second sensor that is disposed at a predetermined distance from the first sensors and senses movements of the examinee; a controller that performs a berg balance test on movements of the examinee on the basis of information sensed and transmitted by the first sensors and the second sensor; and a display that receives berg balance test guide and test result information from the controller and outputs the information through images.

5 Claims, 9 Drawing Sheets

(56) References Cited

U.S. PATENT DOCUMENTS

2016/0076930 A1\* 3/2016 Sakai .................... G01G 19/44
  177/1
2016/0128642 A1\* 5/2016 Barralon .............. A61B 5/6823
  600/592

\* cited by examiner

BERG BALANCE TESTING APPARATUS AND METHOD FOR THE SAME

BACKGROUND OF THE INVENTION

Field of the Invention

The present invention relates to a berg balance testing apparatus and method and, more particularly, a berg balance testing apparatus and method that can obtain an accurate berg balance testing result without a skilled tester.

Description of the Related Art

In general, the weak and elderly is a word indicating old people over the age of 65 or weak people. The weak and elderly, in most cases, has weak muscles and bones, so they have difficulties in taking exercise such as common weight training, swimming, jogging, and cycling. If they take exercise, the elderly cannot exercise for a long time because it is hard on joints. Further, they may be injured or their own diseases may get worse when they take exercise in a wrong way.

On the other hand, a berg balance test is a test that can check items such as walking ability evaluation, balance ability evaluation, estimation of an injury from a fall, and evaluation of performance ability of movements in daily life.

The berg balance test is intended for old people with poor balance ability and patients with a stroke, a spinal cord injury, and Parkinson's disease, and old people and patients with poor walking ability.

The test performs evaluation of fourteen items pertaining to standing, sitting, and changing positions on patients by a physical therapist or a doctor and gives a total of 56-point measured in the unit of 5-point (0-point to 4-point), in which 0-point means that performance is impossible and 4-point means that independent performance is possible, and the-points are summed up.

However, according to the berg balance test of the related art, since physical therapists and doctors take patients as objects, they may make different determinations and the total-points may be different depending on the subjective views of the testers, so the examination results are not objective. Further, testers have to input the evaluation result-points into a computer separately from the test, so it takes a long time. Further, since experts have to perform the test in person, it takes large costs.

CITATION LIST

Patent Literature

Korean Patent Application Publication No. 2002-0095314

SUMMARY OF THE INVENTION

The present invention has been made in an effort to solve the problems and an object of the present invention is to provide a berg balance testing apparatus and method that allows a patient who is subject to a berg balance test to perform the test by himself/herself while seeing a monitor screen with minimum help of a tester.

In order to achieve the objects of the present invention, a berg balance testing apparatus for testing movement ability in daily life of an examinee according to an aspect of the present invention includes: a floor frame that is a stage on which the examinee takes movements; a plurality of first sensors that is disposed in sections divided to have a predetermined area on the floor frame and senses positions of the feet of the examinee; a second sensor that is disposed at a predetermined distance from the floor frame and senses movements of the examinee; a controller that performs a berg balance test on movements of the examinee on the basis of information sensed and transmitted by the first sensors and the second sensor; and a display that receives berg balance test guide and test result information from the controller and outputs the information through images.

Preferably, the apparatus further includes a speaker that receives information from the controller and outputs guide information and test result to the examinee using a voice.

Preferably, the plurality of first sensors are pressure sensors or weight sensors that sense pressure or weight by load.

Preferably, handrail frames that the examinee can hold or lean on are disposed at both sides of the floor frame.

Preferably, the handrail frame includes: a handrail bar that is formed by curvedly integrating two vertical portions and a horizontal portion connecting the upper ends of the two vertical portions; and a flange that has a seat in which the lower ends of the two vertical portions are inserted such that they can rotate at an angle of 3 degrees or less, and is fixed to the floor frame to support the handrail bar.

The handrail bar is disposed to be able to rotate about a direction parallel with the horizontal portion.

Through-holes are formed in the vertical portions and the seat and rotary pins are inserted in the through-holes with the vertical portions inserted in the seat.

In order to achieve the objects, a berg balance testing method according to another aspect of the present invention in which movements for examining movement ability in daily life of an examinee are made on a floor frame divided into a plurality of footboards having a predetermined area, includes the steps of: instructing the examinee to put both feet on predetermined footboards on the floor frame; measuring the weight of the examinee by measuring weight applied to the footboards; measuring changes in the entire weight and in weight of left and right footboards when the examinee makes movements corresponding to test items; and inducing an evaluation point in accordance with a predetermined program on the basis of the changes in the entire weight and in weight of the left and right footboard.

Preferably, in the measuring of changes in the entire weight and in weight of left and right footboards, the method further includes a condition in which weight is not sensed on footboards except for the left and right footboards.

Preferably, the method further includes a step of sensing a movement change of the examinee through a motion sensor.

In order to achieve the objects, a berg balance testing method according to another aspect of the present invention in which movements for examining picking up an object on a floor in a standing position of an examinee are made on a floor frame divided into a plurality of footboards having a predetermined area, includes the steps of: instructing the examinee to put shoes and both feet on predetermined footboards on the floor frame; measuring the weight of the shoes and the examinee by measuring weight applied to the footboards; measuring changes in the entire weight, in weight of left and right footboards, and in weight of the footboard with the shoes thereon when the examinee pick up the shoes; and inducing an evaluation point in accordance with a predetermined program on the basis of the changes in the entire weight, in weight of the left and right footboards, and in weight of the footboard with the shoes thereon.

DETAILED DESCRIPTION OF THE PREFERRED EMBODIMENTS

Figure 1:
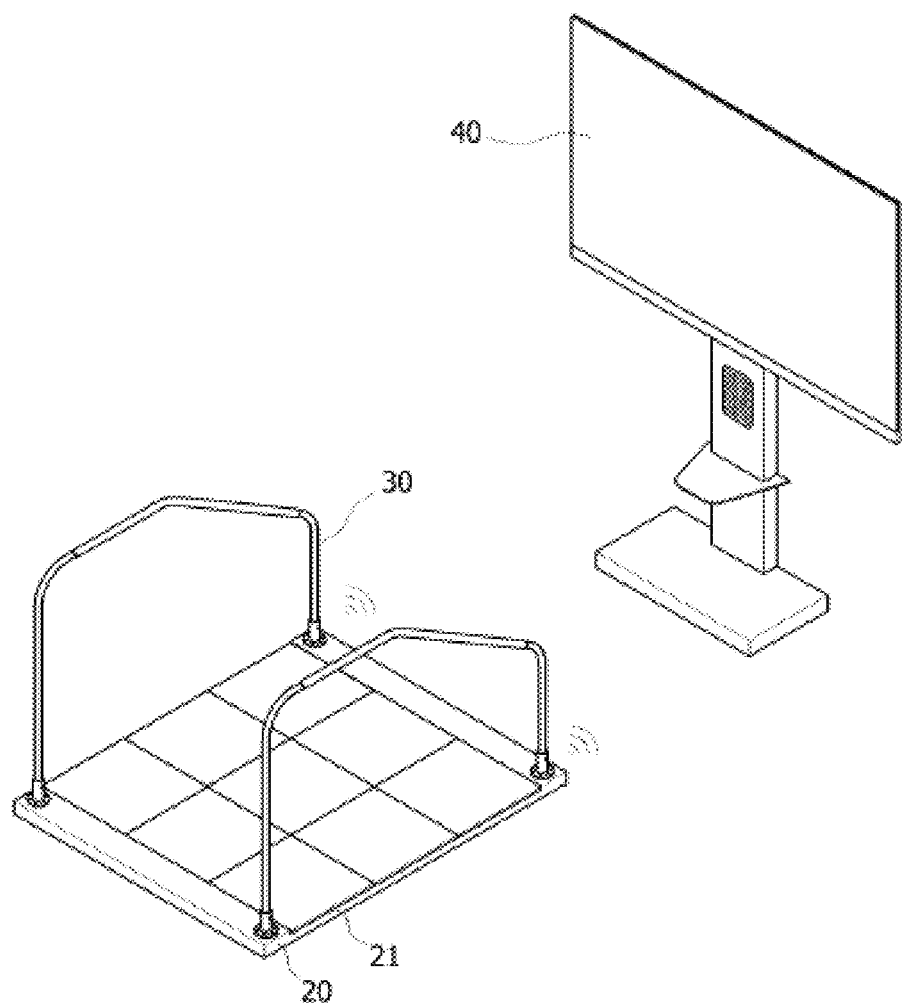
FIG. 1 is a perspective view showing the entire configuration of a berg balance testing apparatus according to the present invention.

The present invention will be described more fully with reference to the accompanying drawings, in which exemplary embodiments of the invention are shown. As those skilled in the art would realize, the described embodiments may be modified in various different ways, all without departing from the spirit or scope of the present invention. In the accompanying drawings, portions unrelated to the description will be omitted in order to obviously describe the present invention, and similar reference numerals will be used to describe similar portions throughout the present specification.

It will be further understood that the terms "comprises" or "have" used in this specification, specify the presence of stated features, steps, operations, components, parts, or a combination thereof, but do not preclude the presence or addition of one or more other features, numerals, steps, operations, components, parts, or a combination thereof. When an element such as a layer, a film, a region, and a plate is "on" another component, it can be directly on the other element or intervening elements may be present therebetween. In contrast, when an element such as a layer, a film, a region, and a plate is "under" another component, it can be directly under the other element or intervening elements may be present therebetween.

A berg balance testing apparatus according to an embodiment of the present invention is described in detail hereafter with reference to the drawings.

A berg balance testing apparatus according to a first embodiment of the present invention, as shown in FIGS. 1 to 6, is a berg balance testing apparatus for testing movement ability in daily life of an examinee and includes a floor frame 20, a plurality of first sensors 21, a second sensor 50, a controller 60, and a display 40.

Referring to FIGS. 1 to 6, the floor frame 20, which is a stage where the examinee makes movements, is a flat stage. An examinee makes movements on the stage in accordance with instructions shown on the display 40 and a test is performed in this process.

All sensors are operated on the basis of the floor frame 20, so the examinee has to make given test movements on the floor frame 20 for accurate berg balance testing.

The floor frame 20 may be made of metal or synthetic resin and may be made of a transparent or translucent material.

It is preferable to make the floor frame 20 thin so that an examinee does not feel inconvenience when he/she gets on and down the floor frame 20.

The plurality of first sensors 21 are floor sensors, which are arranged in sections divided in predetermined areas on the floor frame 20 and sense the positions of feet of an examinee.

It is preferable that the plurality of first sensors are pressure sensors that sense pressure by load or sensors that sense weight.

The number of the plurality of first sensors 21 may be increased in proportion to the number of the sections, and the more the first sensors, the more minutely the movements of an examinee can be sensed, but the number is appropriately determined in consideration of economical efficiency.

Referring to FIGS. 1 to 6, the second sensor 50 is a motion sensor that is disposed at a predetermined distance from the floor frame 20 and senses motions of an examinee.

The second sensor 50 senses motions of an examinee by sensing whether the examinee is sitting or standing and even sensing motions of the arms and legs of a patient.

Referring to FIG. 1, the second sensor 50 is disposed on a frame where the display 40 is installed at a predetermined distance from the floor frame 20. Obviously, the installation position can be changed in accordance with situations.

Referring to FIGS. 1 to 6, the controller 60 performs a berg balance test on movements of an examinee on the basis of sensing information transmitted from the plurality of first sensors 21 and the second sensor 50.

Figure 6:
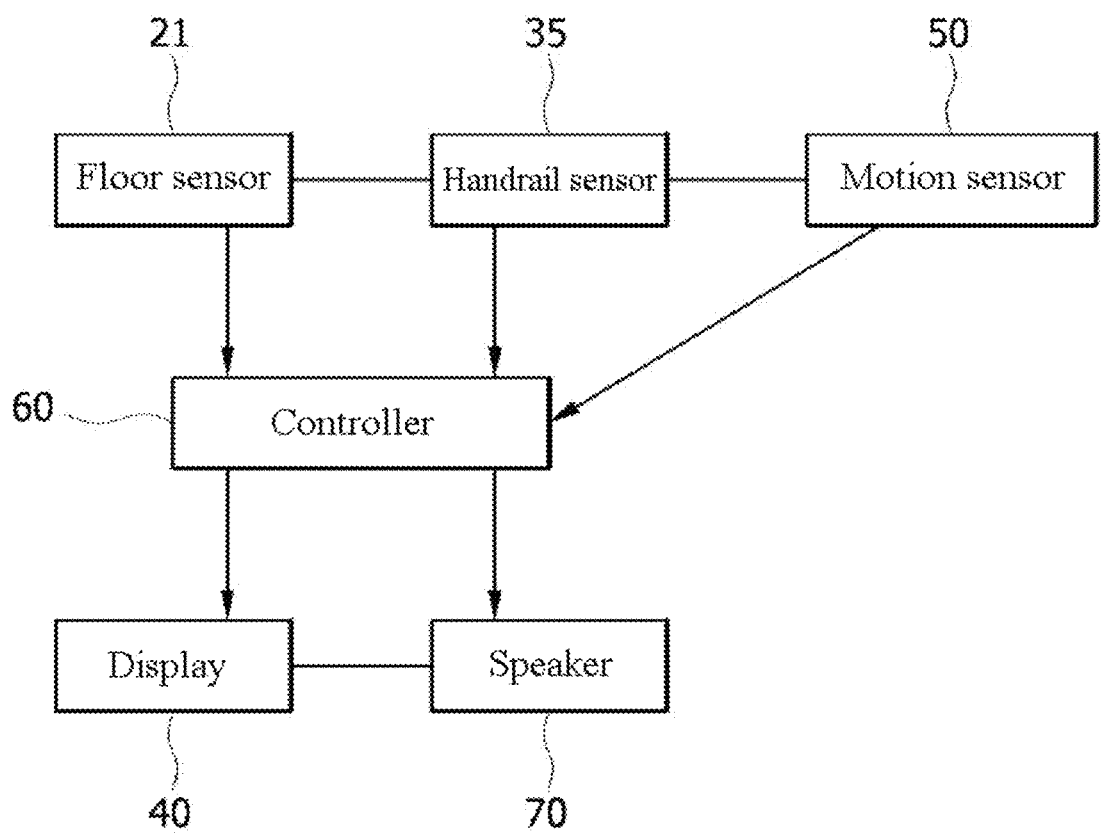
FIG. 6 is a block diagram showing the configuration of a berg balance testing apparatus according to the present invention.

Referring to FIG. 6, the controller 60 receives information from the sensors, performs a berg balance test in accordance with a program that is input in advance, and outputs the test result through the display 40 and a speaker 70.

That is, the controller 60 is an important component in which an algorithm for the berg balance test is actually executed and test determination is performed.

The controller 60 is a computing system including a common microprocessor, and referring to FIG. 1, the controller 60 is disposed in the frame of the display 40.

The controller 60 can be connected to the sensors 21 and 35 on the floor fame 20 through a wire or wirelessly, and in this case, it is connected to the sensors wirelessly not to interfere with movements of an examinee.

It is preferable that an input unit is connected to the controller 60. The input unit may input test start or other information of an examinee. Further, the input unit may use the display 40 as a touch screen and a manager may input information remotely or at a predetermined distance.

Referring to FIGS. 1 to 6, the display 40 receives berg balance test guide and test result information from the controller 60 and outputs them in images.

Referring to FIG. 1, the display 40 is disposed at a predetermined distance from the floor frame 20. Accordingly, an examinee can take movements in accordance with instructions that are output in images while seeing the display 40, and can check the test result later.

The speaker 70 is disposed at a lower portion of the display 40, receives information from the controller 60, and outputs guide information and test result to an examinee through a voice.

Referring to FIGS. 1 to 5, handrail frames 30 are disposed on both sides of the floor frame 20 so that an examinee can hold or lean on the handrail frames.

The handrail frame 30 includes a handrail bar 31 and a flange 32.

The handrail bar 31 is formed by curvedly integrating two vertical portions and a horizontal portion connecting the upper ends of the two vertical portions.

It is preferable to cover the handrail bar 31 with rubber to prevent slip.

It is preferable to use a material such as common stainless steel for the handrail bar 31.

The flange 32 has a seat 32a in which the lower ends of the two vertical portions are inserted such that they can rotate at an angle or 3 degrees or less, and is fixed to the floor frame 20 through a frame portion 32b, thereby supporting the handrail bar 31.

The handrail bar 30 is disposed to be able to rotate about a direction parallel with the horizontal portion.

Through-holes 31a and 32c are formed in the vertical portions and the seat 32a and rotary pins 34 are inserted in the through-holes 31a and 32c with the vertical portions inserted in the seat 32a.

A third sensor 35 that senses pressure that is laterally applied by the lower ends of the vertical portions when the handrail bar 31 is rotated is disposed at the lower end inside the seat 32a.

Pressing pins 33 are disposed at the lower ends of the vertical portions to easily press the third sensors 35.

Figure 5:
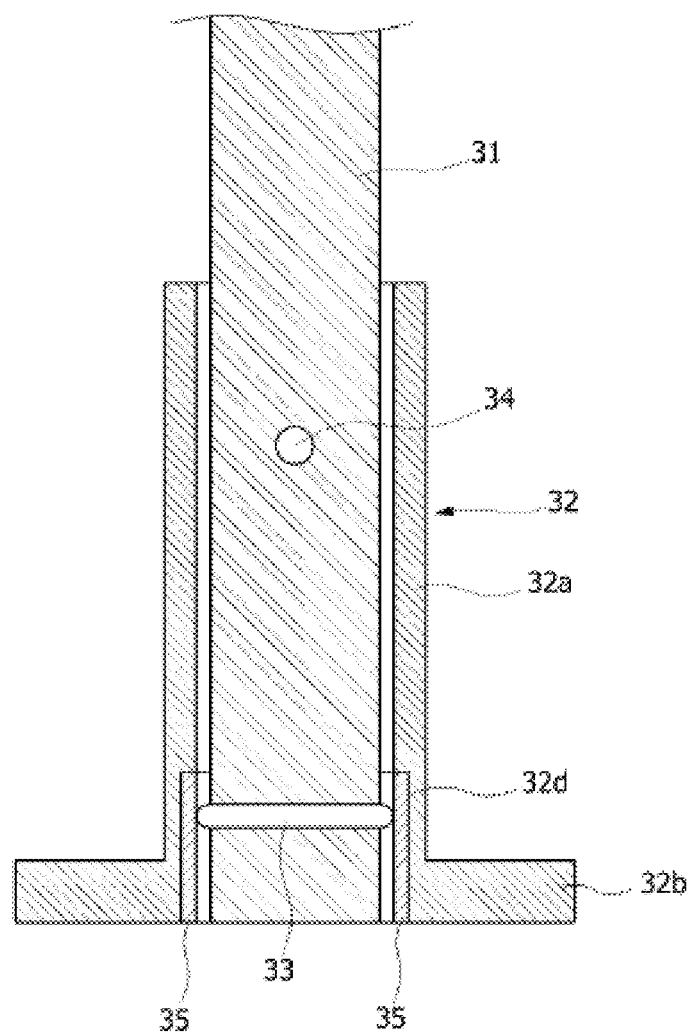
FIG. 5 is a cross-sectional view of the handrail frame that is a component of the berg balance testing apparatus according to the present invention.

According to the structure of the handrail frame 30, referring to FIG. 5, the vertical portions of the handrail bar 31 can rotate within 3 degrees about the rotary pins 34. Further, as the vertical portions are rotated, the pressing pins 33 press the third sensors 35 and corresponding information is transmitted to the controller 60.

The controller 60 determines whether an examinee is leaning on, holding, or not in contact with the handrail frames on the basis of pressure that is transmitted from the third sensors 35 and uses the determination for the berg balance test. That is, when it is determined that a predetermined level or larger pressure is applied to the third sensors 35, it means that an examinee is leaning on or holding the handrail frames 30.

The operation of the berg balance testing apparatus having this configuration according to the present invention is described.

Figure 2:
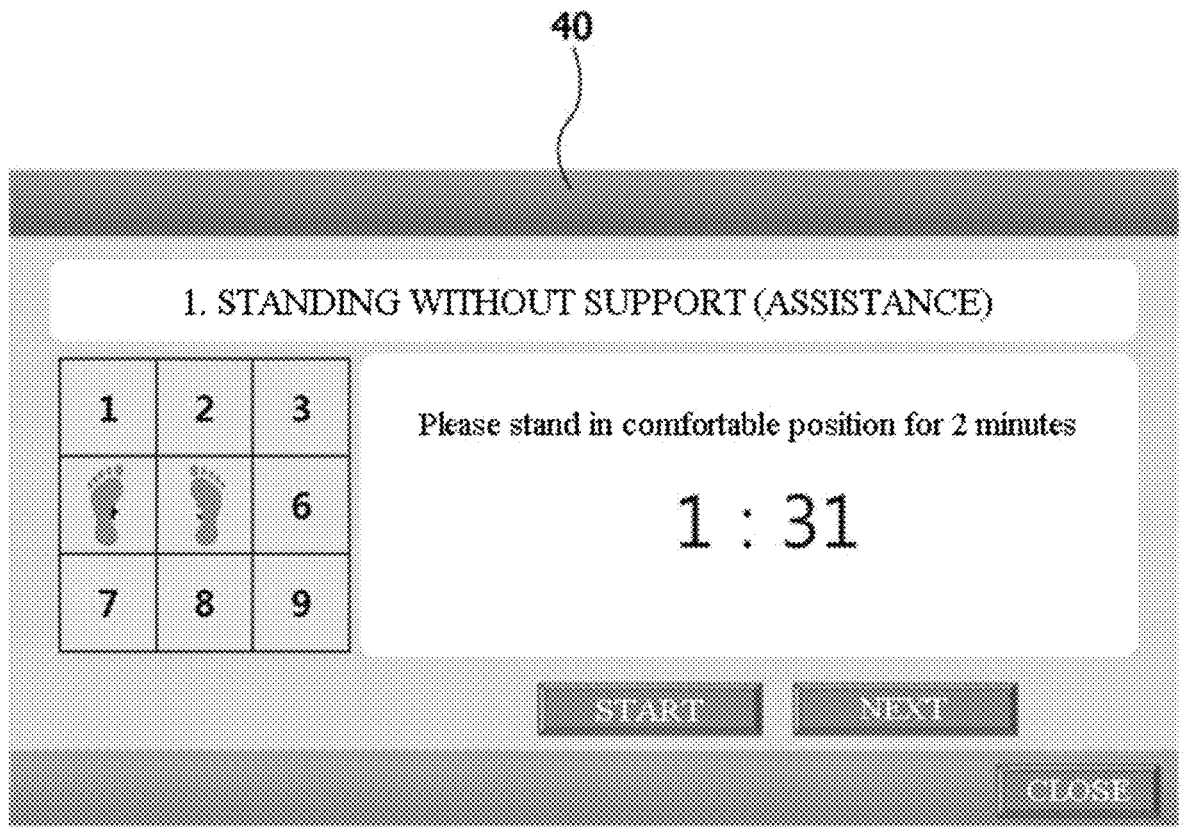
FIGS. 2 and 3 are examples of images shown on a display that is a component of the berg balance testing apparatus according to the present invention.
Figure 3:
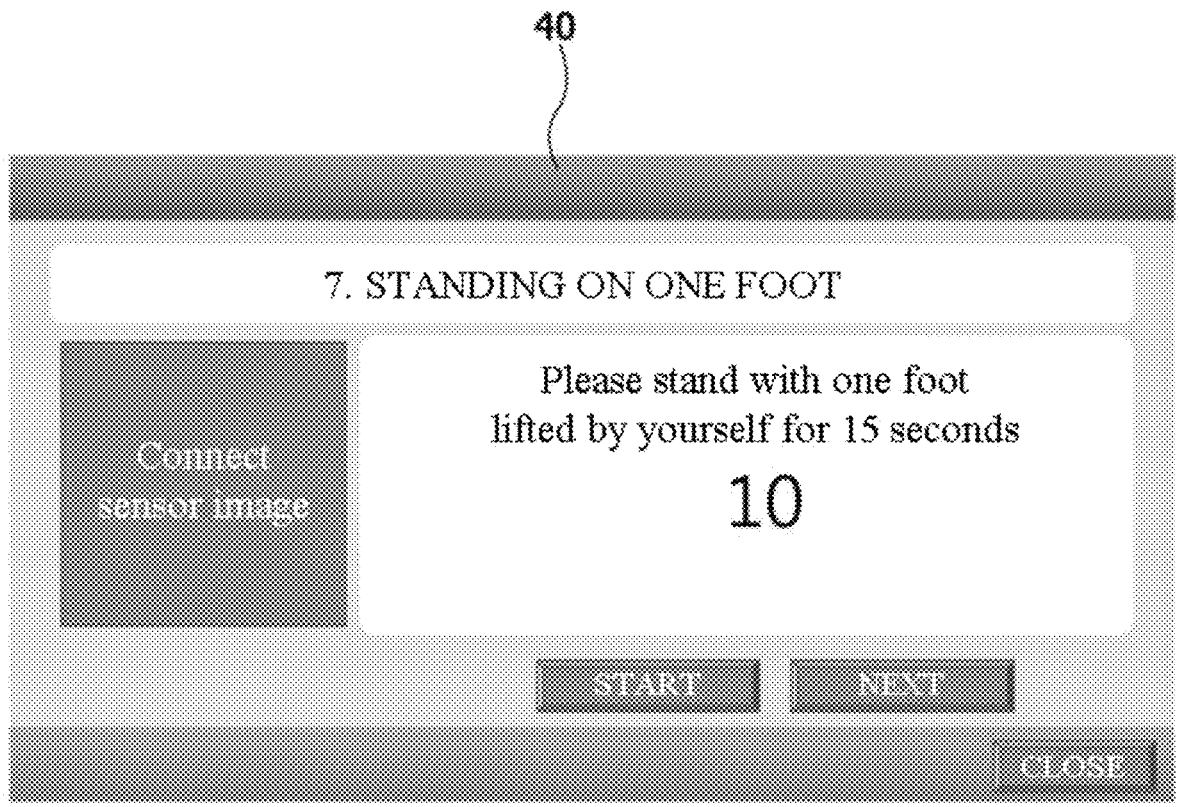
Figure 4:
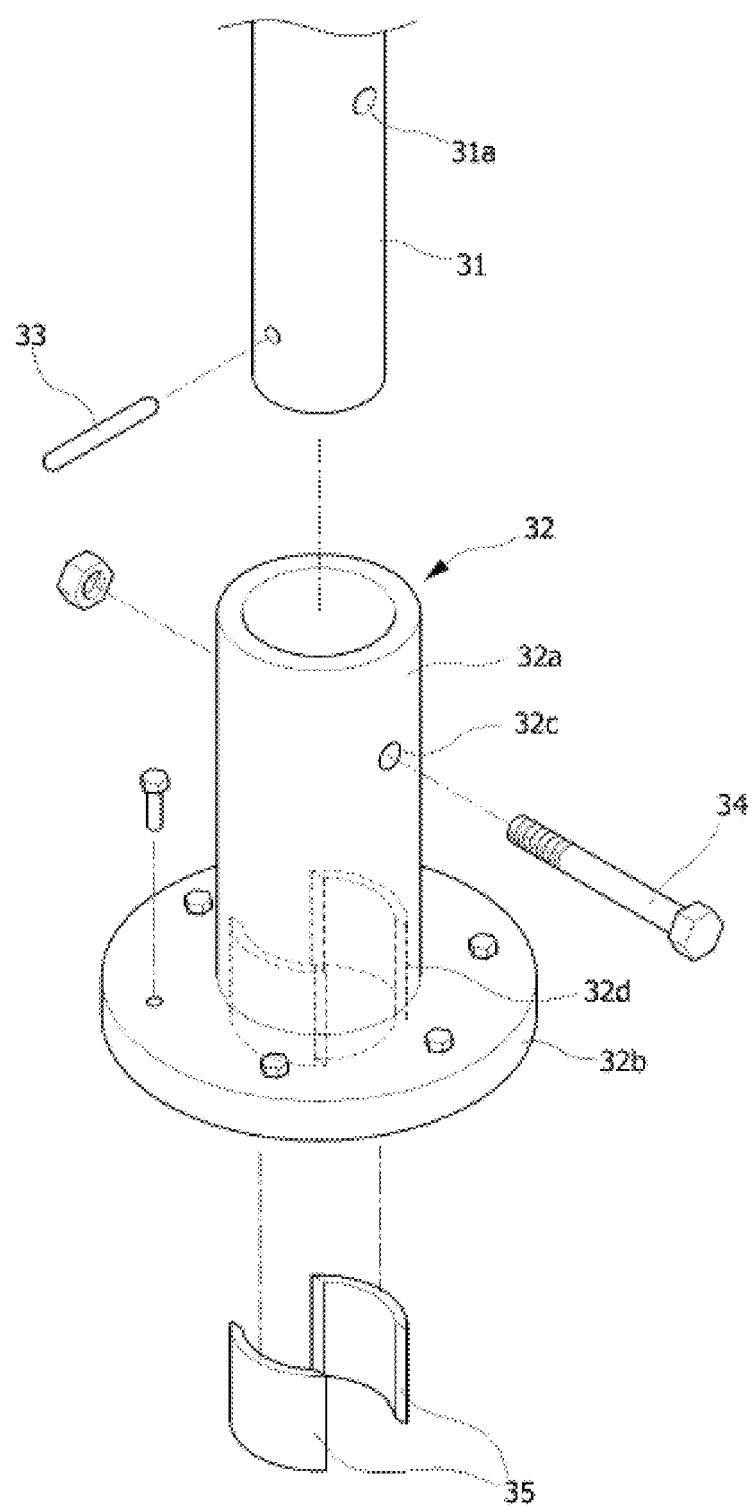
FIG. 4 is an exploded perspective view of a handrail frame that is a component of the berg balance testing apparatus according to the present invention.

First, when a test is started, the controller 60 outputs movements for the test through the display 40, as shown in FIGS. 2 and 3.

The examinee makes movements in accordance with the instructions output through the display 40 and the speaker 70.

The first sensors 21 sense the positions of the feet by measuring the load by the examinee and transmit the corresponding information to the controller 60 and the second sensor 50 senses the movements of the examinee and transmits the corresponding information to the controller 60.

The controller 60 determines whether movements have been normally made on the basis of the information transmitted from the first sensors 21 and second sensor 50 and then gives a point.

That is, a berg balance test that is generally performed proceeds.

The method performs evaluation of fourteen items pertaining to standing, sitting, and changing positions on an examinee and gives a total of 56-point measured in the unit of 5-point (0 to 4-points).

0-point means that performance is impossible and 4-point means that independent performance is possible.

For example, in the case of standing from a sitting position, an instruction "please, stand up without using hands" is output through the display and the speaker.

In this case, 0-point means that medium or maximum help is needed to stand up, 1-point means that minimum help is needed to stand up or keep stably standing, 2-point means that an examinee has stood up using hands after several attempts, 3-point means that an examine can stand up using hands, and 4-point means that an examinee can stand up without using hands and can keep stably standing by himself/herself.

When an examinee holds or leans on the handrail bars using hands, corresponding information is sensed by the third sensors 35 and is transmitted to the controller 60, and the controller 60 uses the information to give points.

According to the test result, the rate of an injury from a fall of examinees with 32-point or less is 20% and the rate of an injury from a fall of examinees with 33 to 36-point is 15.7%. That is, the higher the point, the lower the rate of an injury from a fall.

Figure 7:
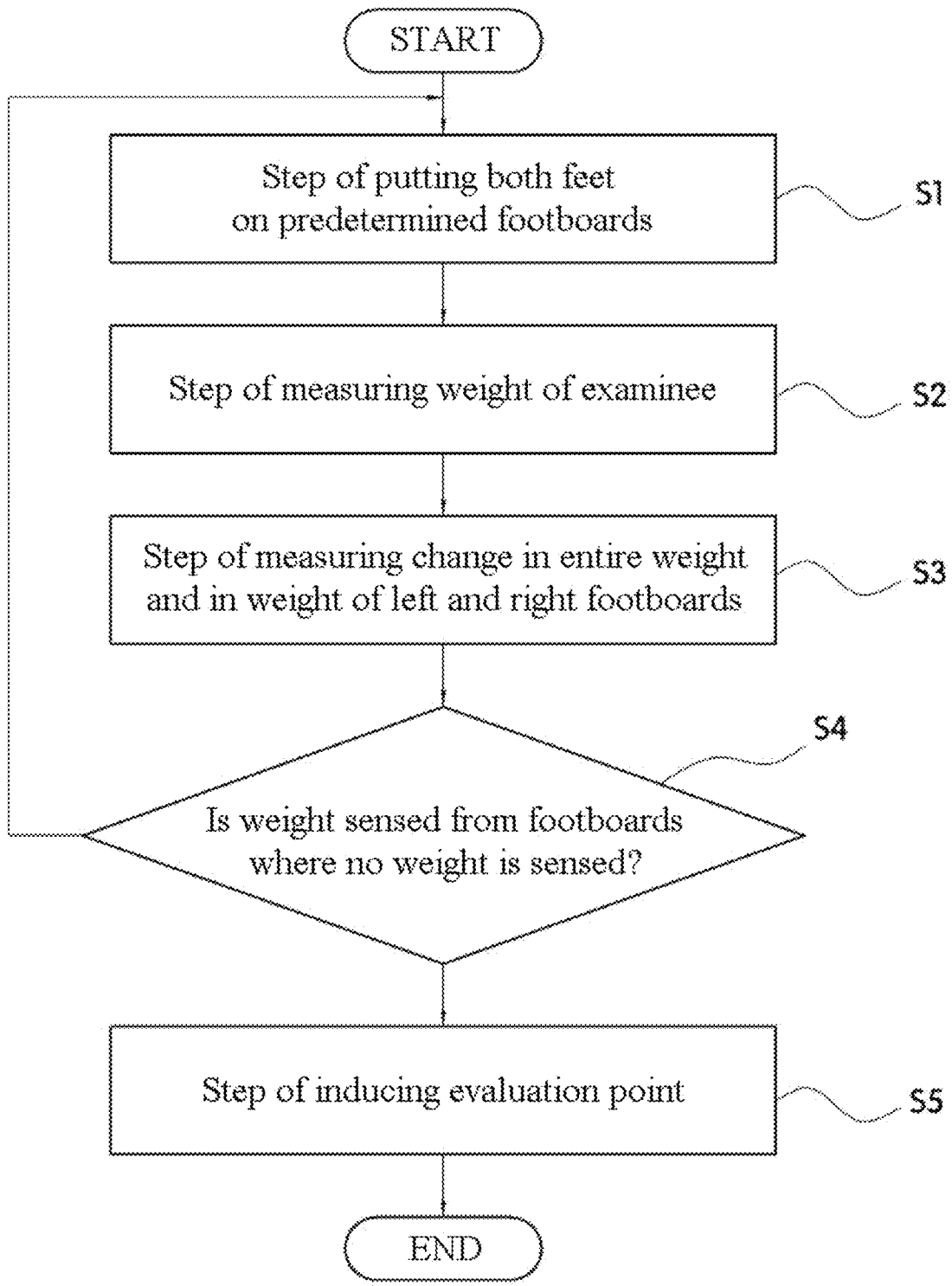
FIG. 7 is a flowchart showing a berg balance testing method according to the present invention.
Figure 8:
FIGS. 8 and 9 show an example of display output by the berg balance testing method according to the present invention.
Figure 8:
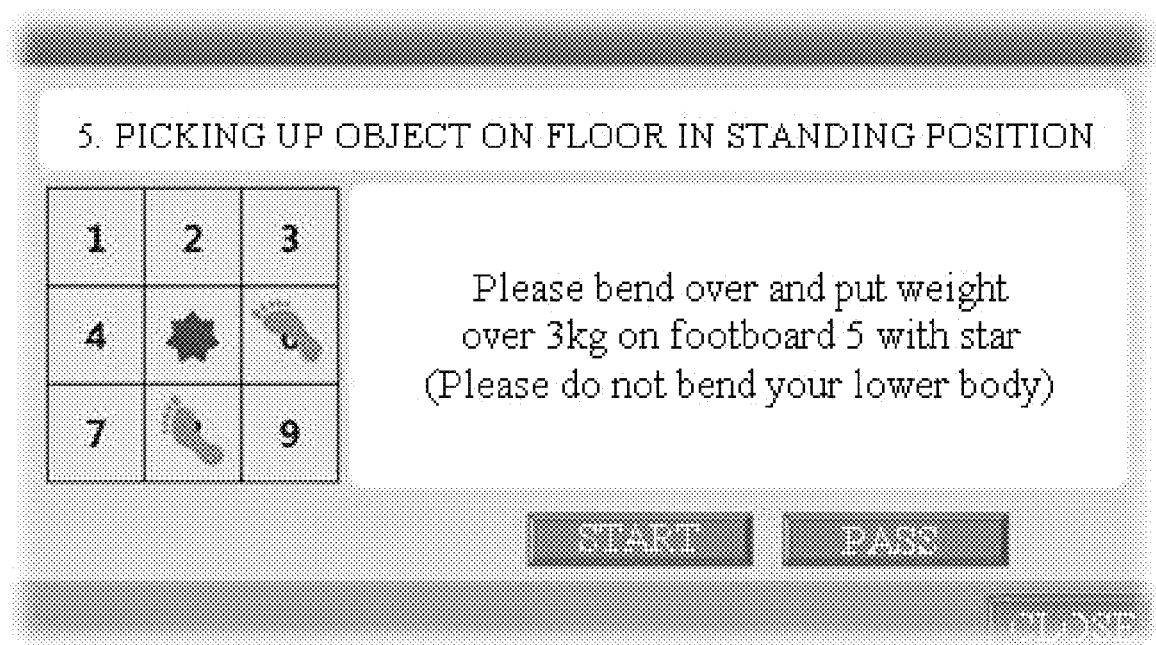
Figure 9:
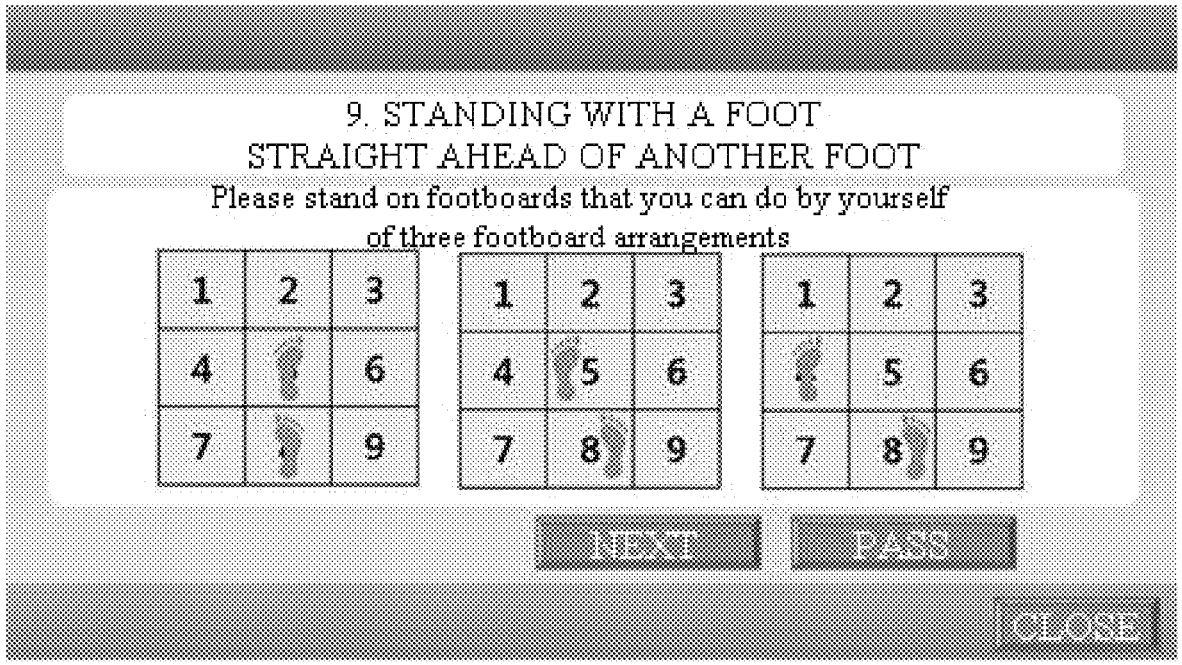
Figure 9:
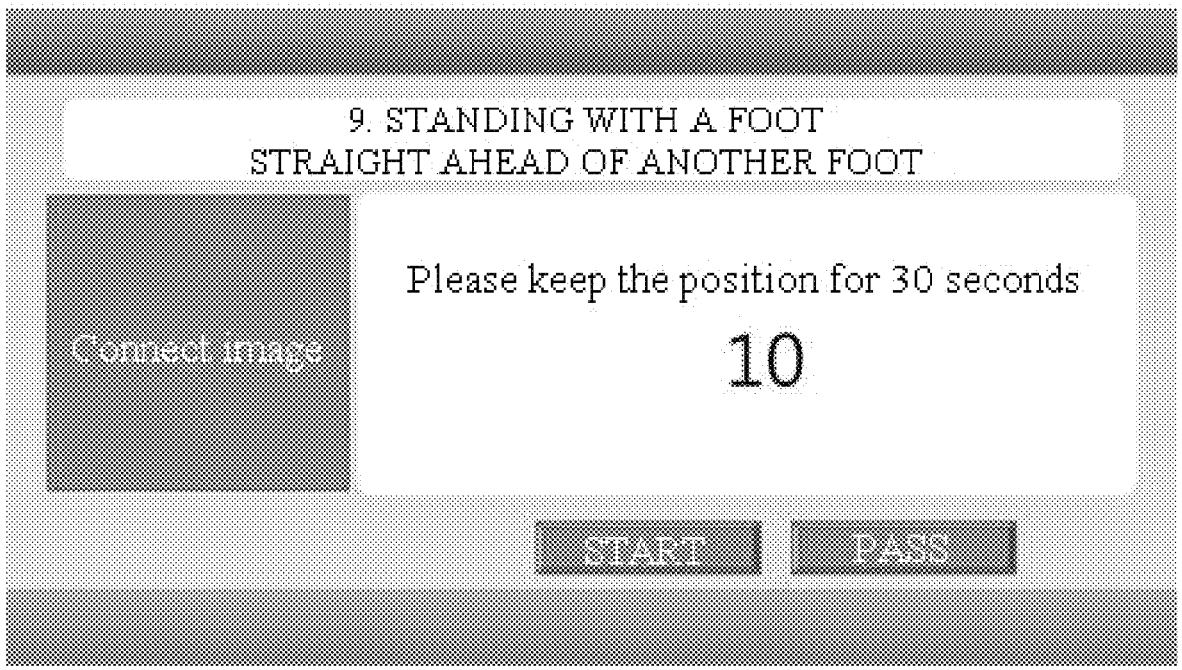

A berg balance testing method according to another embodiment of the present invention is as follows, as shown in FIGS. 7 to 9.

A berg balance testing method according to the present invention in which movements for examining movement ability in daily life of an examinee are made on a floor frame divided into a plurality of footboards having a predetermined area, includes the steps of: instructing the examinee to put both feet on predetermined footboards on the floor frame (S1); measuring the weight of the examinee by measuring weight applied to the footboards (S2); measuring changes in the entire weight and in weight of left and right footboards when the examinee makes movements corresponding to test items (S3); and inducing an evaluation point in accordance with a predetermined program on the basis of the changes in the entire weight and in weight of the left and right footboard (S5).

In order to automatically evaluate the following test items of the berg balance test items, first, the method determines an evaluation point under a condition (option) (S4) in which changes in the entire weight and in weight of the left and right footboards is used and weight is not sensed on other footboards when measurement is performed under predetermined measurement conditions for the test items on the basis of the initial weight of a patient with both feet of the patient on predetermined footboard to perform the test.

The percentages of positive and negative changes may depend on the test equipment and the environment. For example, the method gives points in a test of "standing without support" in a way that when the change of the entire weight is within ±20% for two minutes, which is a test time condition, it gives four out of four and when it is within ±50%, it gives three.

① Standing without support
② Standing without support and with eyes closed
③ Standing without support and with both feet gathered
④ Standing on one foot
⑤ Standing with one foot straight at a side of the other foot
⑥ Stretching arms forward in a standing position
⑦ Alternately putting feet on footboard with a predetermined height A berg balance testing method according to another embodiment of the present invention is as follows, as shown in FIGS. 7 to 9.

In order to automatically evaluate a test item "picking up an object on a floor in a standing position" of the berg balance test items, an examinee is instructed to pick up shoes having a predetermined weight and placed on a predetermined footboard without stepping on another footboard within a predetermined time with the change of the entire weight within a predetermined range.

For example, an examinee is instructed to pick up shoes weighing about 1 kg and placed on a predetermined footboard. 4-point is given when the weight of the reference footboard is close to 0 kg, the change of the weight of the patient is less than 30%, and the movement has been made within 5 seconds, and 3-point is given when the weight of the reference footboard is close to 0 kg, the change of the weight of the patient is less than 30%, and the movement has been made within 10 seconds.

A berg balance testing method according to another embodiment of the present invention is as follows, as shown in FIGS. 7 to 9.

In order to automatically evaluate the following test items of the berg balance test items, the method determines an evaluation point under a condition (option) (S4) in which changes in the entire weight and in weight of the left and right footboards is used and weight is not sensed on other footboards when measurement is performed under predetermined measurement conditions for the test items on the basis of the initial weight of a patient with both feet of the patient on predetermined footboard to perform the test, and by applying all of the conditions on the basis of changes of movements sensed by the motion sensor.

The percentages of positive and negative changes may depend on the test equipment and the environment. For example, in the test of "sitting down from a standing position", for example, when the change of the entire weight reduces by 50% from the weight measured on a footboard at the start of a test, the motion sensor senses the position of a patient who has sat down from the standing position, and 4-poing is given when this movement has been made within 10 seconds, and when these conditions are made within 20 seconds, 3-point is given.

① Sitting down from a standing position
② Sitting down without a back and with feet on a footboard or a floor
③ Standing up from a sitting position
④ Moving Although embodiments of the present invention were described above, the spirit of the present invention is not limited to the embodiment provided herein. Further, those skilled in the art may easily propose other embodiments by adding, changing, and removing components within the scope of the present invention, but they are also included in the scope and spirit of the present invention.

The present invention described above has the following effects.

(1) According to the present invention, since a berg balance test is performed by an apparatus including sensors and a controller, it is possible to achieve more objective and accurate test.

(2) According to the present invention, since not only a pressure sensor and a motion sensor, but sensors are disposed on handrails, it is possible to more clearly check movements of an examinee, so it is possible to provide more accurate test.

While the present invention has been described with respect to the specific embodiments, it will be apparent to those skilled in the art that various changes and modifications may be made without departing from the spirit and scope of the invention as defined in the following claims.

What is claimed is:

1. A berg balance testing apparatus for testing movement ability in daily life of an examinee, the apparatus comprising:
    a floor frame that is a stage on which the examinee takes movements;
    a plurality of first sensors that is disposed in sections divided to have a predetermined area on the floor frame and senses positions of the feet of the examinee;
    a second sensor that is disposed at a predetermined distance from the first sensors and senses movements of the examinee;
    a controller that performs a berg balance test on movements of the examinee on the basis of information sensed and transmitted by the first sensors and the second sensor; and
    a display that receives berg balance test guide and test result information from the controller and outputs the information through images,
    wherein handrail frames that the examinee can hold or lean on are disposed at both sides of the floor frame, and
    wherein the handrail frame includes:
    a handrail bar that is formed by curvedly integrating two vertical portions and a horizontal portion connecting the upper ends of the two vertical portions; and
    a flange that has a seat in which the lower ends of the two vertical portions are inserted such that they can rotate at an angle of 3 degrees or less, and is fixed to the floor frame to support the handrail bar.

2. The apparatus of claim 1, further comprising a speaker that receives information from the controller and outputs guide information and test result to the examinee using a voice.

3. The apparatus of claim 1, wherein the first sensors are pressure sensors or weight sensors that sense pressure or weight by load.

4. The apparatus of claim 1, wherein the handrail bar is disposed to be able to rotate about a direction parallel with the horizontal portion.

5. The apparatus of claim 1, wherein through-holes are formed in the vertical portions and the seat, and rotary pins are inserted in the through-holes with the vertical portions inserted in the seat.

* * * * *